(12) United States Patent
Wagner, III (10) Patent No.: US 7,958,888 B2
(45) Date of Patent: Jun. 14, 2011

(54) CIRCULATION APPARATUS AND METHOD FOR USE OF SAME

(76) Inventor: Fred A. Wagner, III, Ophir, CO (US)

( * ) Notice: Subject to any disclaimer, the term of this patent is extended or adjusted under 35 U.S.C. 154(b) by 1467 days.

(21) Appl. No.: 11/277,129

(22) Filed: Mar. 21, 2006

(65) Prior Publication Data

US 2006/0212103 A1 Sep. 21, 2006

Related U.S. Application Data (60) Provisional application No. 60/663,995, filed on Mar. 21, 2005.

(51) Int. Cl.
*A62B 18/10* (2006.01)
*A62B 17/00* (2006.01)

(52) U.S. Cl. .............. 128/201.28; 128/201.29

(58) Field of Classification Search ............ 128/200.24, 128/200.29, 201.13, 201.22, 201.27–201.29, 128/202.11, 205.26; 2/2.11, 2.14–2.16, 68, 2/93, 97, 272; 601/148–152
See application file for complete search history.

(56) References Cited

U.S. PATENT DOCUMENTS

| | | | | |
|---|---|---|---|---|
| 3,138,155 A | * | 6/1964 | Bould ................... | 128/201.27 |
| 3,343,536 A | * | 9/1967 | Brisson et al. ........... | 128/202.11 |
| 3,675,244 A | * | 7/1972 | Mayo et al. ........... | 2/2.16 |
| 3,763,497 A | * | 10/1973 | Leach ................. | 2/81 |
| 4,245,631 A | | 1/1981 | Wilkinson et al. | |
| 4,294,242 A | * | 10/1981 | Cowans .................. | 128/201.13 |
| 4,417,574 A | * | 11/1983 | Talonn et al. ........... | 128/205.12 |
| 4,981,134 A | | 1/1991 | Courtney | |
| 5,303,425 A | * | 4/1994 | Mele .......................... | 2/115 |
| 5,364,678 A | | 11/1994 | Lumb et al. | |
| 5,490,501 A | * | 2/1996 | Crowley ................ | 128/204.17 |
| 6,082,025 A | * | 7/2000 | Bonk et al. ........................ | 36/29 |
| 6,289,890 B1 | * | 9/2001 | Bliss et al. ............. | 128/203.11 |
| 6,302,094 B1 | | 10/2001 | Wehrly et al. | |
| 6,415,453 B1 | * | 7/2002 | Anderson et al. ................ | 2/458 |
| 6,584,969 B2 | * | 7/2003 | Farmer .................... | 128/200.22 |
| 6,789,540 B1 | | 9/2004 | Lin | |
| 6,805,118 B2 | * | 10/2004 | Brooker et al. .......... | 128/203.12 |
| 6,996,848 B2 | | 2/2006 | Donaldson | |
| 2005/0279351 A1 | | 12/2005 | Lewis et al. | |
| 2007/0240716 A1 | * | 10/2007 | Marx ....................... | 128/204.21 |

\* cited by examiner

*Primary Examiner* — Kristen C Matter
(74) *Attorney, Agent, or Firm* — Scott T. Griggs; Griggs Bergen LLP (57) ABSTRACT

A circulation apparatus and method for use of the same are disclosed. In one embodiment, tubing provides gas communication between an air intake portion disposed at a first end and a breathing sub-apparatus at a second end. A bladder, which may be incorporated into a clothing garment or sleeping gear, is coupled to the tubing between the first and second ends. At least one valve is disposed within the tubing in order to selectively allow gas communication from the air intake portion to the breathing sub-apparatus and selectively allow gas communication from the breathing sub-apparatus to the bladder. Following an inhalation, heated exhaled air is circulated through the bladder to maintain a healthy core temperature and prevent hypothermia.

13 Claims, 6 Drawing Sheets

CIRCULATION APPARATUS AND METHOD FOR USE OF SAME

PRIORITY STATEMENT & CROSS-REFERENCE TO RELATED APPLICATIONS

This application claims priority from U.S. Patent Provisional Application No. 60/663,995, entitled "Body Heat Capture Bladder Incorporated Into Cold Weather Garments and Sleeping Gear" and filed on Mar. 21, 2005, in the name of Fred A. Wagner, III; which is hereby incorporated by reference for all purposes.

TECHNICAL FIELD OF THE INVENTION

This invention relates, in general, to circulation apparatuses and, in particular, to a circulation apparatus and method for use of the same that circulates heated exhaled air to maintain a healthy core temperature and prevent hypothermia.

BACKGROUND OF THE INVENTION

Hypothermia is a medical condition in which an individual's core body temperature drops significantly below normal and the individual's metabolism begins to be impaired. Typically, hypothermia begins to occur when the core body temperature drops below 95° F. (35° C.). At its worst, untreated hypothermia can result in collapse or death.

In cold conditions, varying degrees of inadequate shelter or protection from cold and water, fatigue, and insufficient food may combine to cause hypothermia. In remote and rugged locations, where individuals are undertaking physically demanding activities such as hiking, outdoor camping, and mountain climbing, for example, conserving resources and preventing hypothermia are critically important. Accordingly, a persistent need exists for apparatuses and methods that better conserve resources and enable individuals to maintain a healthy core temperature and prevent hypothermia.

SUMMARY OF THE INVENTION

A circulation apparatus and method for use of the same are disclosed that circulate heated exhaled air through a bladder to maintain a healthy core temperature and prevent hypothermia. In one embodiment, tubing provides gas communication between an air intake portion disposed at a first end and a breathing sub-apparatus at a second end. A bladder, which may be incorporated into an outdoor article of manufacture such as clothing or sleeping gear, for example, is coupled to the tubing between the first and second ends. At least one valve is disposed within the tubing in order to selectively allow gas communication from the air intake portion to the breathing sub-apparatus and selectively allow gas communication from the breathing sub-apparatus to the bladder.

BRIEF DESCRIPTION OF THE DRAWINGS

For a more complete understanding of the features and advantages of the present invention, reference is now made to the detailed description of the invention along with the accompanying figures in which corresponding numerals in the different figures refer to corresponding parts and in which.

DETAILED DESCRIPTION OF THE INVENTION

While the making and using of various embodiments of the present invention are discussed in detail below, it should be appreciated that the present invention provides many applicable inventive concepts which can be embodied in a wide variety of specific contexts. The specific embodiments discussed herein are merely illustrative of specific ways to make and use the invention, and do not delimit the scope of the present invention.

Figure 1:
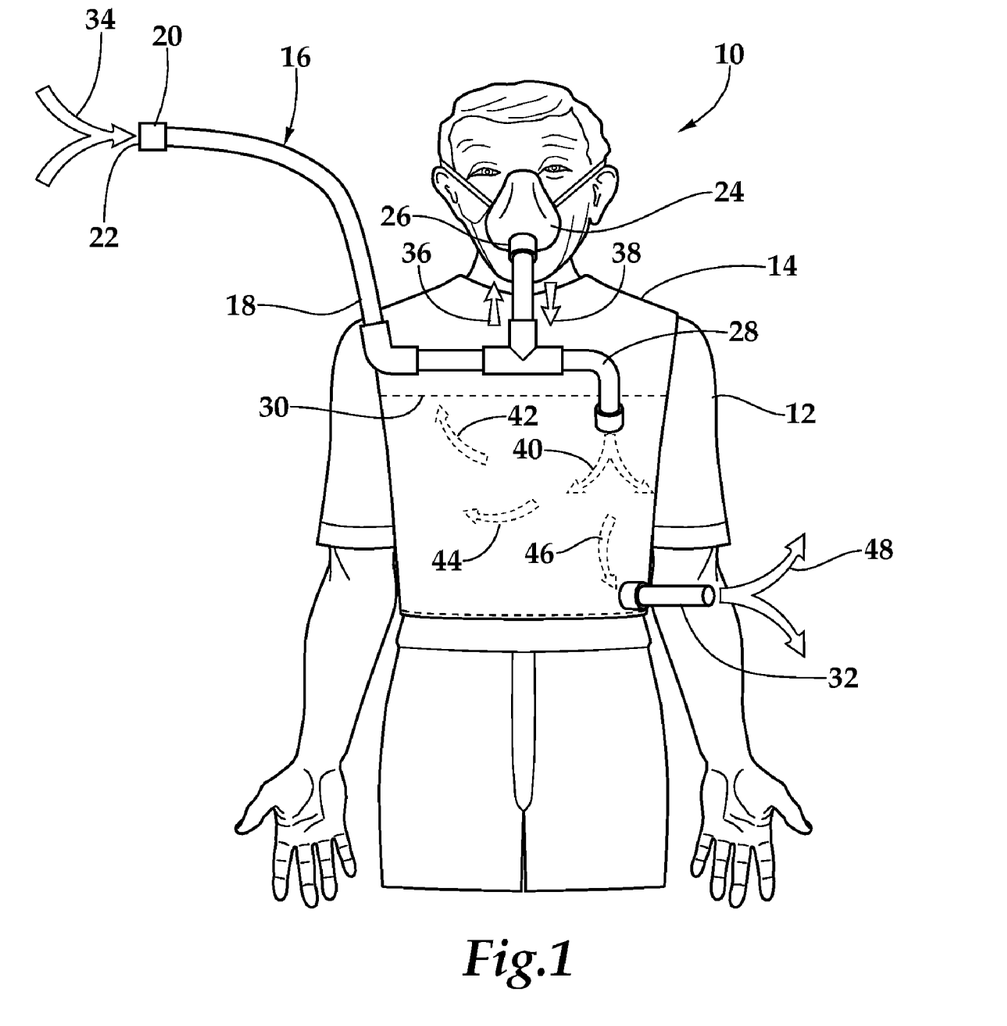
FIG. 1 is a front perspective view of one embodiment of a circulation apparatus incorporated into an article of clothing being utilized by an individual.

Referring initially to FIG. 1, therein is depicted one embodiment of a circulation apparatus 10 that is being utilized by an individual 12 wearing clothing including an article of clothing which is depicted as a vest 14. Tubing 16, which includes a main branch tube 18, provides gas communication between an air intake portion 20 disposed at a first end 22 of the tubing 16 and a breathing sub-apparatus at a second end 26 of the tubing 16. The breathing sub-apparatus is illustrated as a mask 24 which is operable to be worn on the face of the individual 12.

A secondary branch tube 28 coupled to the tubing 16 between the first and second ends 22, 26 couples a bladder 30 to the main branch tube 18. The bladder 30 is incorporated into the vest 14 and is appropriately ghosted. As will be discussed and illustrated in further detail hereinbelow, at least one valve is disposed within the tubing 16, which as discussed the includes main branch tube 18 and the secondary branch tube 28, in order to selectively allow both gas communication from the air intake portion 22 to the breathing sub-apparatus and from the breathing sub-apparatus to the bladder 30. Additionally, an exhaust valve and an axillary tube 32 are associated with the bladder 30 to selectively allow gas and fluid communication between the interior and exterior of the bladder 30.

In operation, the circulation apparatus 10 utilizes respiratory pressure and heat to circulate exhaled air around the body to maintain core body temperature. More specifically, the individual 12 inhales and breathes in cold air from the exterior of the circulation apparatus 10 by way of the air intake portion 20, tubing 16, and the mask 24 as represented by arrows 34, 36. Once inhaled, the air is respirated and the exhaled air, which has a temperature greater than the inhaled air, is circulated through the bladder 30 by way of the mask 24 and tubing 16 as represented by arrows 38-46. After the air is circulated, the air is exhausted through the auxiliary tube 32 as shown by arrows 48. The circulated exhaled air warms the core body temperature of the individual 12.

Figure 8:
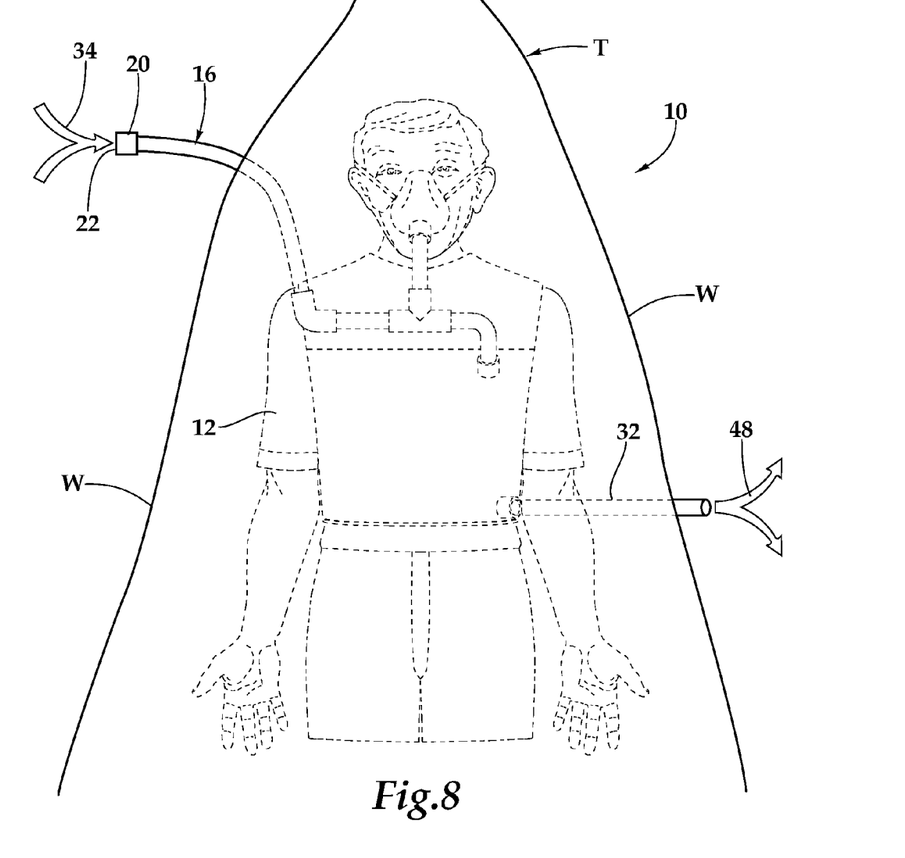
FIG. 8 depicts a front perspective view of one embodiment of a circulation apparatus incorporated into an article of clothing and tent being utilized by an individual.

It should be appreciated that although the circulation apparatus 10 is depicted as being incorporated into a vest, the circulation apparatus 10 presented herein may be used independently of the vest or other article or the circulation apparatus may be used with an article other than a vest. For example, the circulation apparatus 10 may be employed with an outdoor article of manufacture such as a jacket or other clothing. Further, the circulation apparatus may be employed with a blanket, a sleeping bag, a foot bag, a hand warmer, a tent (T) having sidewalls (W)—as shown in FIG. 8, or some combination thereof including combinations with one or more articles of clothing, for example.

Figure 2A:
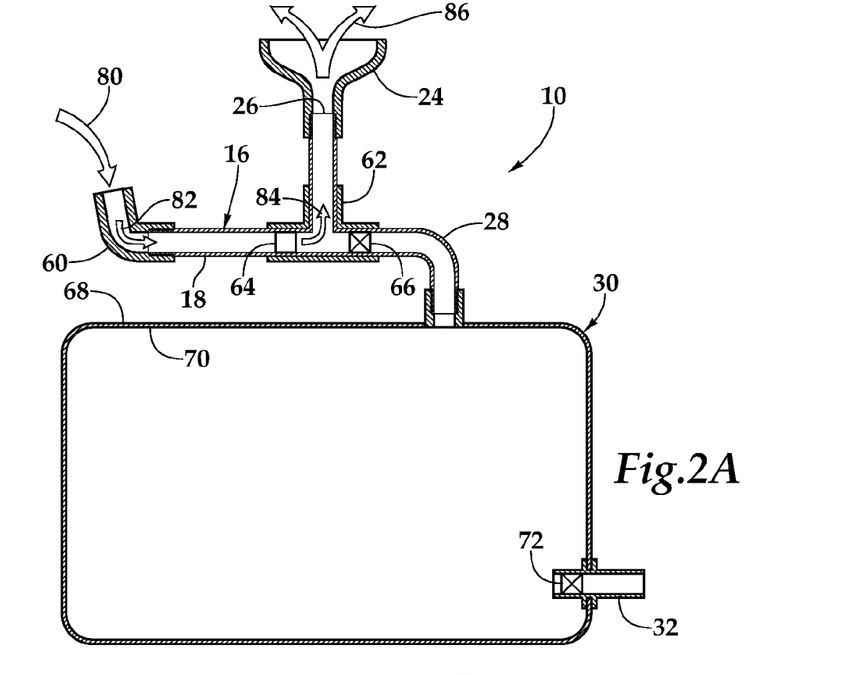
FIG. 2A is a cross-sectional view of the circulation apparatus in a first operational mode illustrating an air intake segment.

FIG. 2A depicts the circulation apparatus 10 in further detail. As previously discussed, the circulation apparatus 10 includes the tubing 16 which connects the air intake valve 20 to the mask 24 as well as the mask 24 to the bladder 30. In one implementation, the tubing 16 comprises a tubular, flexible or semi-flexible polymer material with suitable insulation to prevent heat loss. The polymer material may have additional properties such as anti-bacterial properties. It should be appreciated that other materials such as metal alloys may be used in the construction of the tubing 16 as well as components associated with the tubing 16. Further, the tubing 16 may have a large enough diameter to eliminate back pressure.

The mask 24 is constructed of materials similar to the tubing 16. Additionally, the mask 24 is of a size and shape to conform to the face of the individual and provide a snug, close fit. In one implementation, an elastic band is used to secure the mask 24 to the head of the individual 12. The circulation apparatus 10 may be one integral piece or comprise a component construction that permits the circulation apparatus 10 to be easily assembled and disassembled. The component construction also permits certain components to be replaced as a result of wear-and-tear through normal use. As illustrated, the tubing 16 is a multi-component piece including quick connecting joints 60, 62, for example.

As previously discussed, the circulation apparatus 10 includes at least one valve for regulating the flow air within the circulation apparatus 10. As depicted, the circulation apparatus includes two valves 64, 66 within the tubing 16. The valve 64, which may be considered the "cold air" valve, permits cold to be pulled through the tubing 16 and the valve 66, which may be considered a "warm air" valve permits exhaled air to be expelled through the secondary branch 28 of the tubing 16 into the bladder 30 for circulation.

The bladder 30 includes a body 68 defining a cavity 70 for circulating exhaled air. In one implementation, the bladder 30 includes a flexible or semi-flexible material that is non-porous and microbe resistant. An exhaust valve 72 is positioned in the auxiliary tube 32 of the bladder 32 to exhaust air and water vapor from the bladder 32. It should be appreciated that the bladder 30 may be constructed in a number of shape and size configurations and the desired shape and size of the bladder 30 will depend in part on the application of the circulation apparatus 10. For example, the bladder 30 will have one size and shape if it is utilized in a pocket of a sleeping bag and another size and shape if it is utilized with hand warmers. Further, it should be appreciated that the circulation apparatus 10 may include any number of air intake portions, valves, masks, and bladders. Further, the positioning of the components may vary from what is depicted. For example, the "cold air" valve may be positioned closer to the air intake portion and the "warm air" valve may be positioned closer to the bladder or the mask.

As depicted in FIG. 2A, the circulation apparatus 10 is in a first operational mode wherein the individual 12 is inhaling air of a first temperature, which may be cold air if the circulation apparatus is being used in an outdoor, remote location. As depicted by arrows 80-86, air is inhaled into the air intake portion 20 and travels through the valve 64 in the tubing 16. The inhalation opens the valve 64 to selectively allow gas communication from the air intake portion 20 to the mask 24. Further, the inhalation closes the valve 66 to selectively prevent gas communication from the air intake portion 20 to the bladder 30. The inhaled air travels through the tubing 16 to the mask 24 where it is respirated in the individual's lungs.

Figure 2B:
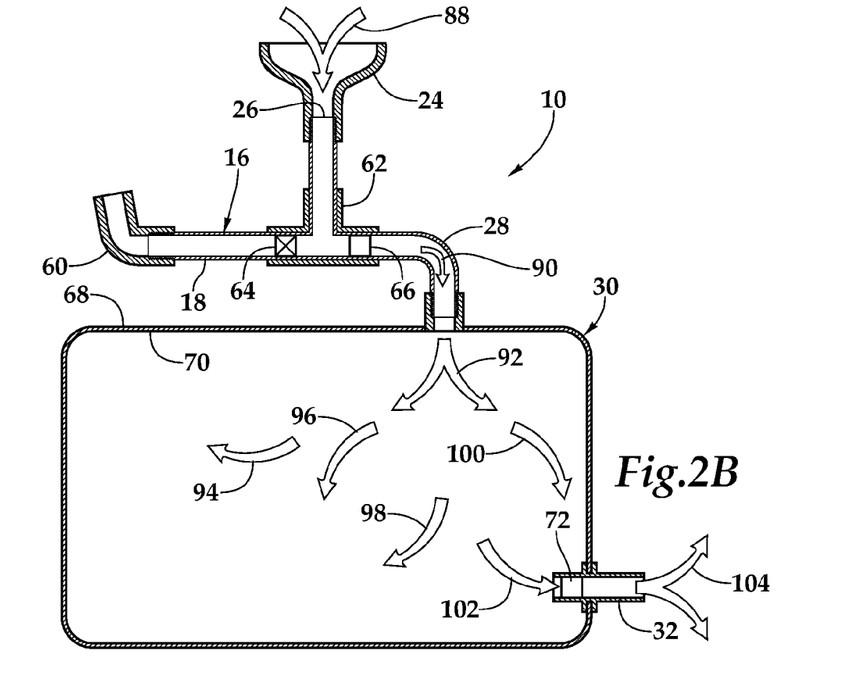
FIG. 2B is a cross-sectional view of the circulation apparatus in a second operational mode illustrating an air exhaust segment.

FIG. 2B depicts the circulation apparatus 10 in a second operational mode wherein the individual 12 is exhaling the air. As previously discussed, the air the individual 12 is exhaling is of a higher temperature than the air inhaled due to the respiration process. The exhalation of air closes the valve 64 to selectively prevent gas communication from the mask 24 to the air intake portion 20. On the contrary, the exhalation of air opens the valve 66 in order to selectively allow gas communication from the mask 24 to the bladder 30. Similarly, the exhalation of air opens the valve 72 to selectively allow fluid communication from the interior to the exterior of the bladder 30.

As depicted by arrows 88-104, the exhaled air travels from the mask 24 through the tubing 16 to the bladder 30 where the air is circulated before exiting the bladder 30 through the valve 72 and auxiliary tube 32. While the exhaled air is circulating in the cavity 70 of the bladder 30, the heat of the exhaled air is transferred to the body of the bladder 68 and onto the individual 12 in order to heat and sustain the core body temperature of the individual 12.

In addition to air, water vapor in the exhaled air exits the bladder 30 through the valve 72 and the auxiliary tube 32. Moreover, as previously discussed, the bladder 30 includes a compressable and foldable material. Any excess water vapor which is accumulated in the bladder 30 because of respiration may be removed from the bladder 30 by rolling and/or folding the bladder 30.

As illustrated in FIGS. 2A and 2B, the circulation apparatus 10 comprises an air intake segment (see FIG. 2A) and an air exhaust segment (see FIG. 2B). The air intake segment or cold air intake segment is defined by an intake tubing portion, which is the portion of main branch tubing 18 and tubing 16 that connects the air intake portion 20 and the mask 24, as well as the air intake portion 20 and the mask 24. The air exhaust segment or warm air exhaust segment is defined by an exhaust tubing portion, which is the portion of the secondary branch tubing 28 and tubing 16 that connects the mask 24 and the bladder 28, as well as the mask 24 and the bladder 28. An intake valve, which is valve 64, is disposed within the air intake segment for selectively allowing gas communication from the air intake portion 20 to the mask 24. Further, an exhaust valve, which is valve 66, is disposed within the air exhaust segment for selectively allowing gas communication from the mask 24 to the bladder 30. An additional auxiliary exhaust valve, valve 72, is associated with the bladder 30 for selectively allowing air and water vapor to exit the bladder 30.

Figure 3A:
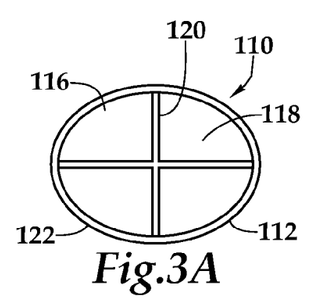
FIG. 3A is a front view of one embodiment of a one-way flap valve in the closed position that may be utilized with the circulation apparatus.
Figure 3B:
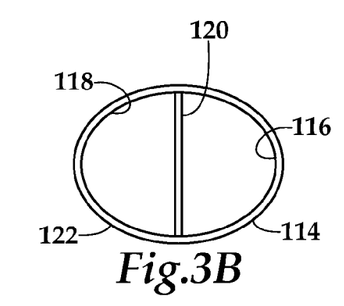
FIG. 3B is a rear view of the one-way flap valve of FIG. 3A in the closed position.
Figure 3C:
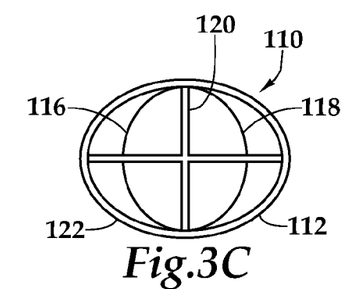
FIG. 3C is a front view of the one-way flap valve of FIG. 3A in an open position.
Figure 3D:
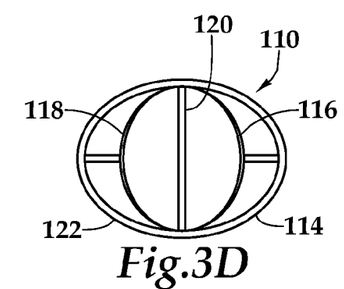
FIG. 3D is a rear view of the one-way flap valve of FIG. 3A in the open position.

FIGS. 3A and 3B depict one embodiment of a one-way flapper valve 110 having sides 112, 114 that may be utilized with the circulation apparatus 10. When in a closed position, flexible membranes 116, 118 are in connection with a cross member 120 and a tension ring 122, thus crating a seal and preventing air or other fluid movement. As best seen in FIGS. 3C and 3D, when the one-way flapper valve 110 is in an open position, the flexible membranes 116, 118 are separated from the tension ring 122, thus allowing air or other fluid movement.

In operation, a one-way flapper valve of the type described in FIGS. 3A through 3D may be utilized as valve 64, valve 66, or valve 72 depicted in FIGS. 2A and 2B. With reference to valve 64, the side 112 is oriented to face the air intake portion 20 and the side 114 is oriented to face the mask 24. With reference to valve 66, the side 114 is oriented to face the bladder 30 and the side 112 is oriented to face the mask 24. Lastly, with respect to the valve 72, the side 114 is oriented to face the exterior of the bladder 30 and the side 112 is oriented to face the interior of the bladder 30.

It should be appreciated that although a one-way flapper valve is illustrated and described, other types of valves may be utilized and are within the teachings of the present invention. For example, one or more of the valves described herein may be ball valves, diaphragm valves, or other flow control devices.

Figure 4:
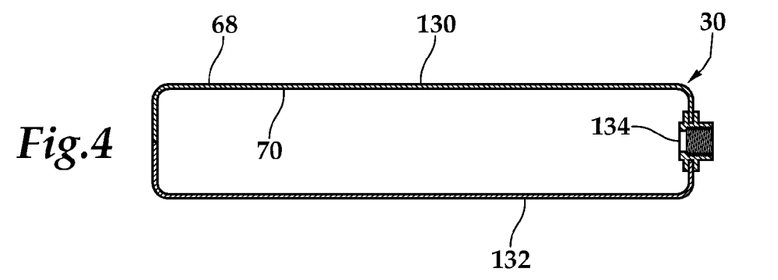
FIG. 4 is cross-sectional view of one embodiment of a bladder that may be utilized with the circulation apparatus.

FIG. 4 depicts one embodiment of the bladder 30 that may be utilized with the circulation apparatus 10. The bladder 30 includes a coupling portion 134 that couples the bladder 30 to the tubing 16. Top and bottom portions 130, 132 may each include different hydrophobic, polymer materials so that the top and bottom portions 130, 132 of the bladder 30 repulse each other and resist adhering to one another.

Figure 5:
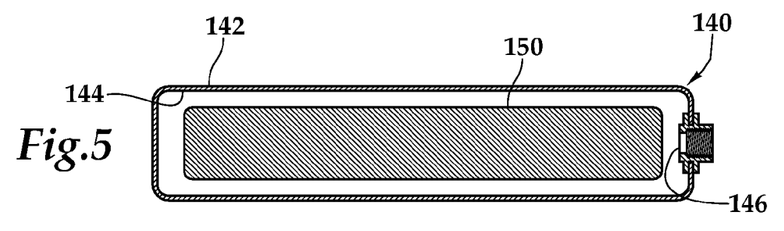
FIG. 5 is a cross-sectional view of another embodiment of a bladder.

FIG. 5 depicts another embodiment of a bladder 140. In this embodiment, the bladder 140 has a body 142 defining a cavity 144. A coupling portion 146 is disposed in the body 142 and the body 142 includes a polymer material which is hydrophobic. A partition 150, preferably comprising a different polymer material than that of the body 142, is disposed within the cavity 144. The polymer material of the body 142 does not adhere to the partition 150. Therefore, the polymer material of the partition 150 prevents the top portion and bottom portion of the body 142 from adhering to each other.

Figure 6:
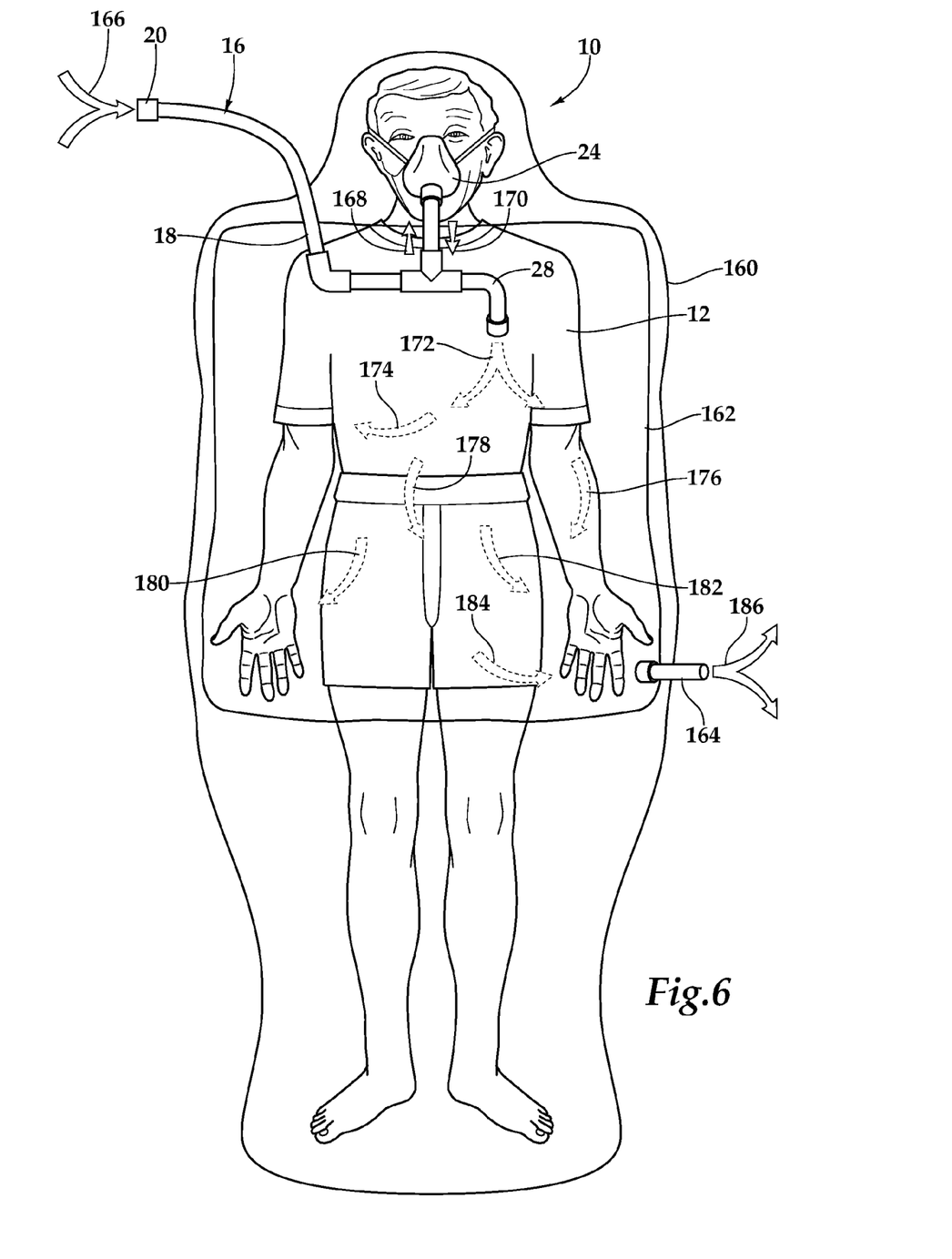
FIG. 6 is a front perspective view of one embodiment of a circulation apparatus incorporated into a sleeping bag being utilized by an individual.

FIG. 6 depicts one embodiment of the circulation apparatus 10 incorporated into a sleeping bag 160 being utilized by the individual 12. The tubing 16 provides gas communication from the exterior to the mask 24. A bladder 162 is also attached to the tubing 16. At least one valve is disposed within the tubing 16 to regulate gas communication therein. Additionally, an exhaust valve is associated with the bladder 162 to permit the expulsion of air and water vapor from the bladder via an auxiliary tube 164. As illustrated, the bladder 162 is incorporated into the lining of the sleeping bag 160. In operation, as shown by arrows 166-186, the circulation apparatus 10 intakes cold air for respiration and captures the warm, respirated air and then holds this air close to the individual's body in the bladder 162 so that the individual 12 may maintain a warm temperature more efficiently. This embodiment, as well as the other embodiments, may be utilized by an individual for short or long durations of time in response to hypothermic conditions. With respect to short durations, for example, the circulation apparatus may be used for a short period of time to dry a wet individual or to quickly warm a cold individual.

As previously discussed, the circulation apparatus may be utilized alone or in conjunction with one or more articles of manufacture such as an expedition tent. When camping using an expedition tent, water vapor in expedition campers' or individuals' exhaled air may freeze in the interior of the tent. Additionally, $CO_2$ may buildup as a result exhaled $CO_2$ becoming trapped in the tent. The circulation apparatus may be utilized with an expedition tent such that both the air intake portion and auxiliary tube are positioned outside the tent. For example, the circulation apparatus may be utilized with the foot bag of a sleeping bag and the air intake portion and auxiliary tube are positioned outside the tent.

In this embodiment, the individual is breathing in fresh, cold air from outside and expelling the respirated air, which includes unwanted byproducts such as water vapor and high levels of $CO_2$, outside of the tent. With this arrangement, the circulation apparatus described herein displays efficacy in mitigating water vapor build up and the consequential freezing inside the expedition tent. Additionally, the circulation apparatus is efficient in preventing $CO_2$ buildup within the expedition tent. In particular, the circulation apparatus permits the individual to be within the shelter of an expedition tent and warmth of a sleeping bag while breathing in fresh, outside air and expelling respirated air outside of the expedition tent.

Figure 7:
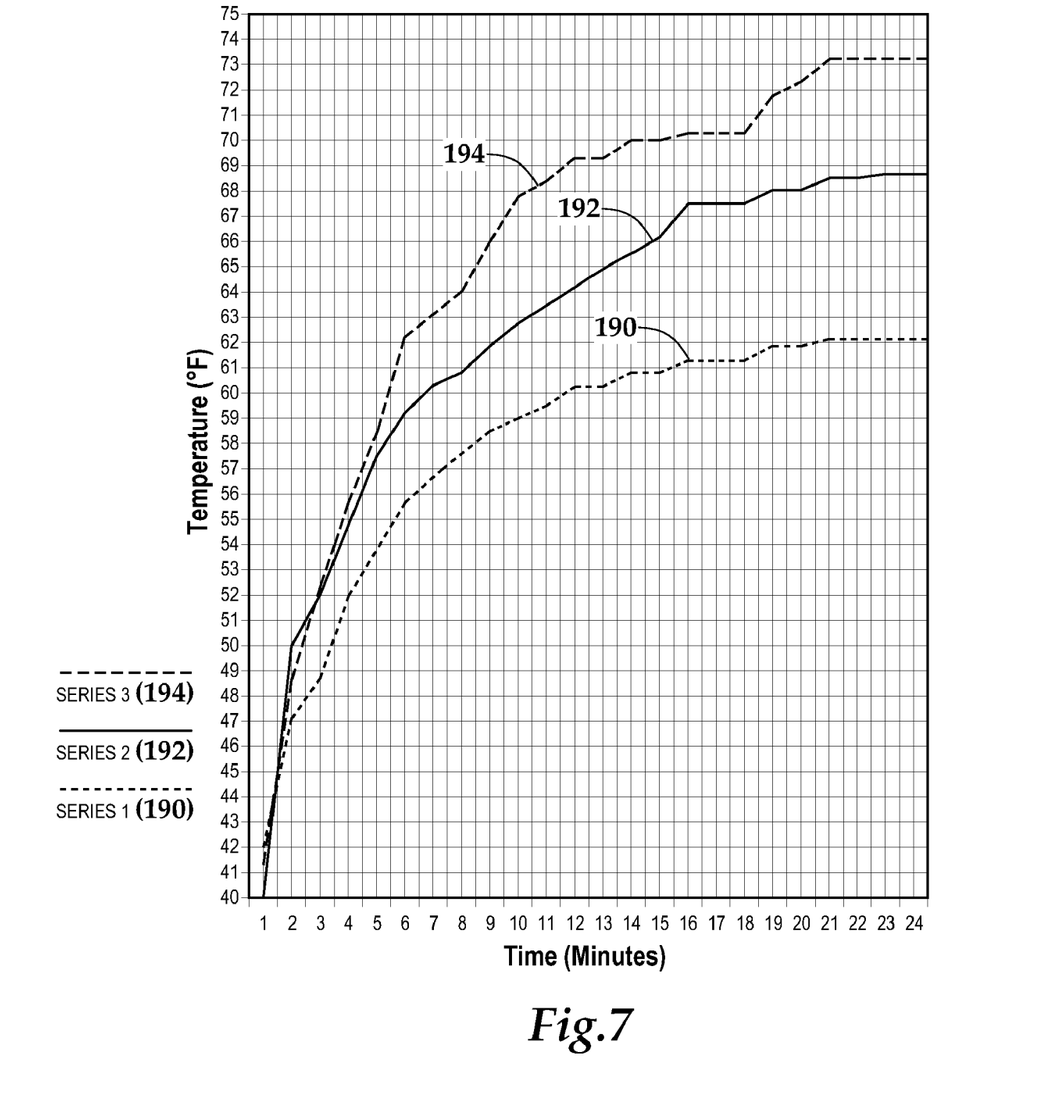
FIG. 7 depicts a graph of temperature versus time illustrating the results of an experiment using two embodiments of the circulation apparatus and a control.

FIG. 7 depicts a graph of temperature versus time illustrating the results of an experiment using two embodiments of the circulation apparatus and a control. The experiment simulated actual use in the field by using three test series protocols; namely Series 1: a control, Series 2: one embodiment of the circulation apparatus, and Series 3: a different embodiment of the circulation apparatus.

In Series 1, which is depicted by line 190, the ambient temperature was 42° F. (5.5° C.) and the subject was positioned in a sleeping bag having a foot bag. The sleeping bag was unzipped and lapped closed. The subject was instructed to breath normally. From a cold start, temperature readings were constantly taken in the sleeping bag for a period of 24 minutes.

In Series 2, which is depicted by line 192, the ambient temperature was 40° F. (4.4° C.). The subject was positioned in a sleeping bag having a foot bag and a circulation apparatus incorporated into the foot bag. The sleeping bag was zipped to 18 inches (45.7 cm) and the subject was instructed to breath normally and as a result, in response to an inhalation, cold air was taken through tubing from an air intake portion to a breathing sub-apparatus secured to the individual's face. In response to an exhalation, air warmed by respiration was moved through the tubing from the breathing sub-apparatus to a bladder incorporated into the foot bag where the air was circulated prior to being exhausted. From a cold start, during this process, the temperature inside the sleeping bag was constantly read for a period of 24 minutes. Additionally, following the testing period, the bladder was examined for residual water vapor.

In Series 3, which is depicted as line 194, the ambient temperature was 40.3° F. (4.6° C.) The subject was positioned in a sleeping bag having a foot bag and a circulation apparatus incorporated into the foot bag. The circulation apparatus of Series 3 included an additional air intake portion and an additional one-way valve as compared to the circulation apparatus of Series 2. The sleeping bag was zipped to 18 inches (45.7 cm) and the subject was instructed to breath normally in a manner similar to that described in Series 2. From a cold start, the temperature inside the sleeping bag was constantly read for the testing period and following the testing period, the bladder was examined for residual water vapor.

As illustrated in the graph of FIG. 7 and Table I: Temperature Test Results for Simulated Field Conditions presented hereinbelow, the Series 2 and 3 protocols utilized embodiments of the circulation apparatus and maintained a higher temperature in the sleeping bag than the Series 1 protocol, which was the control. The markedly higher temperatures of the sleeping bags incorporating the circulation apparatus translated into greater warmth in the sleeping bags and a higher core temperature for the individual. Further, with respect to the Series 2 and 3 testing protocols, the individual noted that the foot bag expanded and contracted with respiration while warming the individual's feet and providing heat to maintain the individual's core body temperature. The feedback, i.e., the movement of the bag and feeling of warmth, provided by the circulation apparatus was reassuring to the individual.

TABLE I

Temperature Test Results for Simulated Field Conditions

|  | Series 1 | Series 2 | Series 3 |
|---|---|---|---|
| TIME | 6 minutes | 6 minutes | 6 minutes |
| TEMPERATURE | 56° F. (13° C.) | 60° F. (15.5° C.) | 62.5° F. (17° C.) |
| PERFORMANCE VERSUS CONTROL | N/A | 7% greater (19% greater) | 12% greater (30% greater) |
| TIME | 12 minutes | 12 minutes | 12 minutes |
| TEMPERATURE | 60° F. (15.5° C.) | 64.5° F. (18° C.) | 69.5° F. (21° C.) |
| PERFORMANCE VERSUS CONTROL | N/A | 7.5% greater (16% greater) | 15.5% greater (35% greater) |
| TIME | 18 minutes | 18 minutes | 18 minutes |
| TEMPERATURE | 61.5° F. (16.5° C.) | 68° F. (20° C.) | 71° F. (21.5° C.) |
| PERFORMANCE VERSUS CONTROL | N/A | 10.5% greater (21% greater) | 15.5% greater (30% greater) |
| TIME | 24 minutes | 24 minutes | 24 minutes |
| TEMPERATURE | 62° F. (16.5° C.) | 68.5° F. (20° C.) | 73° F. (23° C.) |
| PERFORMANCE VERSUS CONTROL | N/A | 10.5% greater (21% greater) | 18% greater (40% greater) |

As illustrated in Table II: Water Vapor Test Results for Simulated Field Conditions presented hereinbelow, the designs of the Series 2 and 3 protocols exhausted all but nominal amounts of water vapor from the bladders.

TABLE II

Water Vapor Test Results for Simulated Field Conditions

|  | Series 2 | Series 3 |
|---|---|---|
| TIME | 24 minutes | 24 minutes |
| WATER VAPOR | Nominal | Nominal |

While this invention has been described with reference to illustrative embodiments, this description is not intended to be construed in a limiting sense. Various modifications and combinations of the illustrative embodiments as well as other embodiments of the invention, will be apparent to persons skilled in the art upon reference to the description. It is, therefore, intended that the appended claims encompass any such modifications or embodiments.

What is claimed is:

1. A system for circulating air, comprising:
   a non-divided bladder;
   a mask operable to be worn on the face of an individual, the mask having a breathing tube extending therefrom;
   a T-junction coupling having a first T-junction branch, a second T-junction branch, and a third T-junction branch,
   the first T-junction branch being connected to the breathing tube extending from the mask,
   the second T-junction branch being connected to an air intake tube,
   the second T-junction branch having a first one-way valve therein, the first one-way valve being configured to allow air to enter the T-junction coupling,
   the third T-junction branch being connected to a bladder intake coupling, the bladder intake coupling opening into the bladder,
   the third T-junction branch having a second one-way valve therein, the second one-way valve being configured to allow air to exit the T-junction coupling;
   a bladder outlet coupling opening from the bladder;
   a tent having a tent wall; and
   a tent exhaust tube extending through the tent wall, the tent exhaust tube being coupled to the bladder outlet coupling so that air exiting the bladder is directed outside of the tent via the tent exhaust tube.

2. The system of claim 1, wherein the third T-junction branch is connected to the bladder intake coupling by a bladder intake tube.

3. The system of claim 1, wherein the bladder intake coupling is the only inlet to the bladder, and wherein the bladder outlet coupling is the only outlet from the bladder.

4. The system of claim 1, wherein the non-divided bladder comprises hydrophobic polymer material for at least some of interior surfaces of the bladder to resist adhesion between the interior surfaces of the bladder.

5. The system of claim 1, wherein the breathing tube extending from the mask is the only inlet and outlet for air going into and out of the mask when the mask is operably worn.

6. The system of claim 1, wherein the bladder outlet coupling has a third one-way valve therein, the third one-way valve being configured to allow air to exit the bladder.

7. A system for circulating air, comprising:
   a non-divided bladder;
   a mask operable to be worn on the face of an individual, the mask having a breathing tube extending therefrom;
   a T-junction coupling having a first T-junction branch, a second T-junction branch, and a third T-junction branch,
   the first T-junction branch being connected to the breathing tube extending from the mask,
   the second T-junction branch being connected to an air intake tube,
   the second T-junction branch having a first one-way valve therein, the first one-way valve being configured to allow air to enter the T-junction coupling,
   the third T-junction branch being connected to a bladder intake coupling, the bladder intake coupling opening into the bladder,
   the third T-junction branch having a second one-way valve therein, the second one-way valve being configured to allow air to exit the T-junction coupling;
   a bladder outlet coupling opening into the bladder;
   a tent having tent walls; and
   a tent exhaust tube extending through at least one of the tent walls, the tent exhaust tube being coupled to the bladder outlet coupling so that air exiting the bladder is directed outside of the tent via the tent exhaust tube.

8. The system of claim 7, further comprising a tent intake tube extending through at least one of the tent walls, the tent intake tube being coupled to the air intake tube so that air entering the T-junction coupling is from outside the tent via the tent intake tube.

9. The system of claim 7, wherein the third T-junction branch is connected to the bladder intake coupling by a bladder intake tube.

10. The system of claim 7, wherein the bladder intake coupling is the only inlet to the bladder, and wherein the bladder outlet coupling is the only outlet from the bladder.

11. The system of claim 7, wherein the non-divided bladder comprises hydrophobic polymer material for at least some of interior surfaces of the bladder to resist adhesion between the interior surfaces of the bladder.

12. The system of claim 7, wherein the breathing tube extending from the mask is the only inlet and outlet for air going into and out of the mask when the mask is operably worn.

13. The system of claim 7, wherein the bladder outlet coupling has a third one-way valve therein, the third one-way valve being configured to allow air to exit the bladder.

* * * * *